United States Patent [19]

Esrock

[11] Patent Number: 4,975,054
[45] Date of Patent: Dec. 4, 1990

[54] DENTAL TOOL

[76] Inventor: Bernard S. Esrock, 320 Dungate, Chesterfield, Mo. 63017

[21] Appl. No.: 339,817

[22] Filed: Apr. 18, 1989

[51] Int. Cl.⁵ ............................................ A61G 17/02
[52] U.S. Cl. ...................................... 433/80; 433/126
[58] Field of Search .................. 433/80, 88, 126, 127; 604/257, 258, 261, 140

[56] References Cited

U.S. PATENT DOCUMENTS

| | | | |
|---|---|---|---|
| 2,215,222 | 9/1940 | Levy | 433/127 X |
| 2,231,969 | 2/1941 | Tifft | 433/126 |
| 3,254,646 | 8/1962 | Staunt et al. | 128/224 |
| 3,516,161 | 6/1970 | Ellman | 433/127 X |
| 3,689,088 | 10/1972 | Austin, Jr. | 32/22 |
| 3,698,088 | 10/1972 | Austin, Jr. | 32/22 |
| 3,874,083 | 4/1975 | Buckley | 32/22 |
| 3,882,638 | 5/1975 | Black | 51/12 |
| 3,972,123 | 8/1976 | Black | 32/58 |
| 4,026,025 | 5/1977 | Hunt | 32/22 |
| 4,068,664 | 1/1978 | Sharp et al. | 128/276 |
| 4,108,178 | 8/1978 | Betush | 128/224 |
| 4,149,315 | 4/1979 | Page, Jr. et al. | 32/22 |
| 4,174,571 | 11/1979 | Gallant | 433/216 |
| 4,184,258 | 1/1980 | Barrington et al. | 433/88 |
| 4,214,871 | 7/1980 | Arnold | 433/216 |
| 4,248,589 | 2/1981 | Lewis | 433/126 X |
| 4,249,899 | 2/1981 | Davis | 433/80 X |
| 4,266,815 | 5/1981 | Cross | 285/330 |
| 4,412,402 | 12/1983 | Gallant | 433/88 |
| 4,462,803 | 7/1984 | Landgraf et al. | 433/88 |
| 4,487,582 | 12/1984 | Warrin | 433/88 |
| 4,494,932 | 1/1985 | Rzewinski | 433/88 |
| 4,495,575 | 1/1985 | Mabille | 433/88 |
| 4,522,597 | 6/1985 | Gallant | 433/216 |
| 4,595,365 | 6/1986 | Edel et al. | 433/216 |
| 4,675,004 | 6/1987 | Hadford et al. | 604/44 |
| 4,676,749 | 6/1987 | Mabille | 433/88 |
| 4,680,026 | 7/1987 | Weightman et al. | 604/33 |
| 4,696,644 | 9/1987 | Goof | 433/125 |
| 4,696,645 | 9/1987 | Saupe et al. | 433/125 |

Primary Examiner—Robert P. Swiatek
Assistant Examiner—Nicholas D. Lucchesi
Attorney, Agent, or Firm—Senniger, Powers, Leavitt and Roedel

[57] ABSTRACT

A dental tool adapted to deliver a mixed stream of two fluids to teeth of a patient. It comprises a nozzle, a hand-piece, and a resiliently flexible clip adapted to releasably retain the nozzle in the hand-piece. The nozzle has an elongate body portion, a proximal end, a distal end, and first and second conduits through the body portion. The conduits define first and second fluid passages. The hand-piece is adapted for delivering a first fluid stream and a second fluid stream through a downstream end of the hand-piece to the proximal end of the nozzle and through the fluid passages and distal end of the nozzle. The clip has a base portion secured to the hand-piece and a contact portion adapted for engaging a contact region of the nozzle's body portion. The clip is adapted for being deflected to disengage the contact portion from the contact region to enable a user to readily remove the nozzle from or insert the nozzle into the hand-piece.

27 Claims, 1 Drawing Sheet

U.S. Patent   Dec. 4, 1990   4,975,054
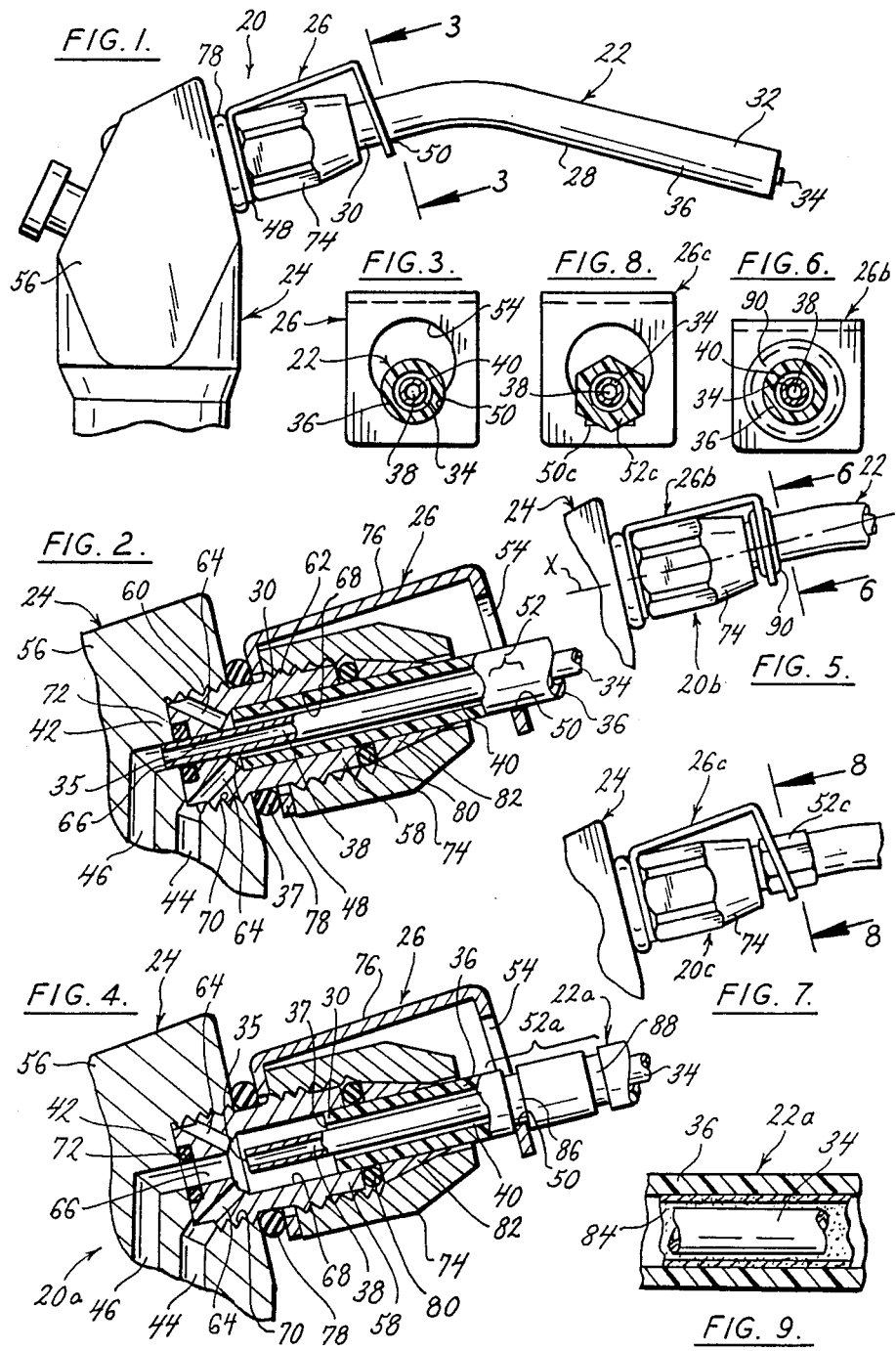

DENTAL TOOL

BACKGROUND OF THE INVENTION

This invention relates to a dental tool, and more particularly to a dental tool adapted to deliver two fluid streams to teeth of a patient.

An air-water syringe is a type of dental tool used by dentists and dental technicians for cleaning debris from a patient's teeth and mouth during a dental procedure. The teeth and mouth are cleaned by the spraying of a water stream, or an air stream, or a mixed air-water stream from the syringe. A typical air-water syringe has a hand-piece and a nozzle releasably attached to the hand-piece. The nozzle is retained in the hand-piece by a retaining collar, attached to a threaded stem in the hand-piece, which compresses an O-ring into a groove on the nozzle. Between uses of the syringe, the nozzle must be removed from the hand-piece and sterilized or be replaced with a sterile nozzle.

Problems encountered with such a syringe are the difficulty in readily removing the nozzle from the hand-piece, cleaning the nozzle and sterilizing it. The retaining collar must be unscrewed from the stem, often requiring a wrench to free the nozzle. Frequently, the stem is frozen against the collar and unscrews from the hand-piece when the collar is turned. Additionally, cleaning and sterilizing such a nozzle is time consuming. Other problems encountered with such a syringe is that the nozzle rotates around its longitudinal axis during use and the air and water streams cannot be mixed prior to entering the nozzle.

SUMMARY OF THE INVENTION

Among the several objects of this invention may be noted the provision of an improved dental tool of the above-described type which includes a nozzle that is readily removable from the hand-piece; the provision of such a dental tool in which the nozzle is prevented from rotating with respect to the hand-piece; the provision of such a dental tool in which the nozzle is of relatively simple and inexpensive construction; and the provision of such a dental tool in which the nozzle is disposable.

Generally, the dental tool of the present invention is adapted to deliver two fluid streams to teeth of a patient. It comprises a nozzle, a hand-piece, and a resiliently flexible clip adapted to releasably retain the nozzle in the hand-piece. The nozzle has an elongate body portion, a proximal end, a distal end, and first and second conduits through the body portion. The conduits define first and second fluid passages. The hand-piece is adapted for delivering a first fluid stream and a second fluid stream through a downstream end of the hand-piece to the proximal end of the nozzle and through the fluid passages and distal end of the nozzle. The clip has a base portion secured to the hand-piece and a contact portion adapted for engaging a contact region of the nozzle's body portion. The clip is adapted for being deflected to disengage the contact portion from the contact region to enable a user to readily remove the nozzle from or insert the nozzle into the hand-piece.

Other objects and features will be in part apparent and in part pointed out hereinafter.

BRIEF DESCRIPTION OF THE DRAWINGS

FIG. 1 is an elevation view of a dental tool constructed according to the principles of the present invention having a hand-piece, nozzle, and clip;

FIG. 2 is an enlarged partial elevation view in partial section showing the nozzle and clip connected to the hand-piece;

FIG. 3 is a cross-sectional view taken along the plane of line 3—3 of FIG. 1;

FIG. 4 is an enlarged partial elevation view in partial section of another embodiment of a dental tool constructed according to the principles of the present invention showing the nozzle in an unseated position;

FIG. 5 is a partial elevation view of another dental tool constructed according to the principles of the present invention in which the clip has an elastomeric annulus for holding the nozzle;

FIG. 6 is a cross-sectional view taken along the plane of line 6—6 of FIG. 5;

FIG. 7 is a partial elevation view of another dental tool constructed according to the principles of the present invention in which the clip has a serrated edge for engaging a region of the nozzle which has a polygonal cross-section;

FIG. 8 is a cross-sectional view taken along the plane of line 8—8 of FIG. 7; and FIG. 9 is a partial elevation view in partial section showing a surface of a conduit of the nozzle coated with a substance.

Corresponding reference numerals indicate corresponding parts throughout the several views of the drawings.

DETAILED DESCRIPTION OF THE PREFERRED EMBODIMENT

A dental tool for delivering a mixed stream of two fluids to teeth of a patient constructed according to the principles of this invention is indicated generally as 20 in FIGS. 1 and 2. The dental tool 20 comprises a nozzle 22, a hand-piece 24, and a resiliently flexible clip 26 adapted for releasably retaining the nozzle 22 in the hand-piece 24.

The nozzle has an elongate body portion 28, a proximal end 30, a distal end 32, and first and second conduits through the body portion 28. The proximal end 30 is adapted for insertion into the hand-piece 24. The first and second conduits, constituting inner and outer conduits 34 and 36, define first and second fluid passages, constituting inner and outer fluid passages 38 and 40. A downstream end 42 of the hand-piece 24 has a first fluid passage 44 for directing an air stream to the outer conduit 36 and a second fluid passage 46 for directing a liquid stream (e.g., water) to the inner conduit 34. Thus, the two fluid streams flow from the passages 44 and 46, through the conduits 34 and 36, and are discharged through the distal end 32. Preferably, the conduits 34 and 36 have coaxial intake ports 35 and 37 at the proximal end of the nozzle 22. The conduits 34 and 36 are held together by the bend (curvature) of the nozzle 22. Thus, the nozzle 22 is simply a tube within a tube which can be constructed easily and inexpensively.

The clip 26 has a base portion 48 secured to the hand-piece 24 and a contact portion 50 adapted to engage a contact region 52 of the nozzle s body portion 28. The clip 26 acts as a spring to bias the contact portion 50 against the contact region 52 to impart a lateral force to the nozzle 22 to frictionally secure the nozzle 22 to the hand-piece 24. As shown in FIG. 3, the clip 26 further includes a generally oblong hole 54, the lower portion of which is defined by the contact portion 50. The upper portion of the hole 54 is generally circular and has a diameter larger than the diameter of the nozzle 22 to enable the clip 26 to be deflected downwardly (with respect to the nozzle 22 as shown in FIG. 3) to disengage the contact portion 50 from the contact region 52. Disengaging the contact portion 50 from the contact region 52 enables a user to readily remove the nozzle 22 from or insert the nozzle 22 into the hand-piece 24.

The hand-piece 24 also includes a handle portion 56 and a stem 58 extending from the handle portion 56. The stem 58 holds both the nozzle 22 and the clip 26. The stem 58 has first and second external screw threads 60 and 62, fluid passages 64, a central bore 66 for receiving a proximal end of the inner conduit 34, and a socket 68 for receiving the nozzle 22. The first screw thread 60 mates with a threaded bore 70 in the handle portion 56 to secure the stem 58 to the handle portion 56. The fluid passages 64 communicate with the passage 44 so that the air stream passes therethrough. When the nozzle 22 is inserted into the hand-piece 24, the proximal end of conduit 34 extends through the central bore 66 so that the inner fluid passage 38 communicates with the second fluid passage 46 of the hand-piece 24. When the proximal end of the conduit 34 extends through the bore 66 it is seated against an O-ring 72 so that the water stream does not mix with the air stream. The proximal end of the conduit being disposed within the bore 66 constitutes a seated position.

The base portion 48 of the clip 26 is firmly held to the hand-piece 24 by a nut 74 screwed to the second screw thread 62. An O-ring 78, preferably made of rubber or the like, is squeezed between the base portion 48 and the handle portion 56 to prevent the clip 26 from rotating on the stem 58. The O-ring 78 also prevents leakage of any fluids from the hand-piece 24. With the base portion 48 firmly held to the hand-piece 24, an intermediate portion 76 of the clip 26 can be deflected to disengage the contact portion 50 from the contact region 52. Another O-ring 80 is positioned over the outer conduit 36 and abuts an end of the stem 58 to prevent leakage of the air stream. The nut 74 urges a generally cone-shaped sleeve 82 against the O-ring 80 to hold the O-ring 80 in place.

FIGS. 4 and 9 show another embodiment of a dental tool, constructed in accordance with the principles of the present invention, designated generally at 20a. The dental tool 20a is similar to the dental tool 20 shown in FIGS. 1-3. Thus, for simplicity, the dental tool 20a has the same reference numerals as the dental tool 20 except for the components that are different which will include the suffix "a". In this embodiment, a nozzle, designated generally at 22a, is positionable between the seated position and an unseated position. When the nozzle 22a is in its seated position, the water stream flows through the inner passage 38 and the air stream flows through the outer passage 40; the fluid streams do not mix prior to being discharged from the distal end 32 of the nozzle 22a. When the nozzle 22a is in its unseated position (as shown in FIG. 4), the air and water streams mix prior to entering the passages 38 and 40. The inner surface of the outer conduit 36 is coated with a water soluble substance 84 (see FIG. 9) such as a concentrated mouthwash or disinfectant. When the nozzle 22a is in its unseated position some of the water from the water stream passes through the outer conduit 36 to dissolve the substance 84 and carry it to the mouth of a patient. When the nozzle 22a is in its seated position, however, the water stream does not pass through the outer conduit 36. Thus, the substance 84 is dissolved when the nozzle 22a is in the unseated position but not when it is in the seated position.

As shown in FIG. 4, the nozzle 22a has first and second circumferential grooves 86 and 88 dimensioned for being engaged by the clip 26. The grooves 86 and 88 constitute the contact region 52a of the nozzle 22a. When the proximal end of the conduit 34 extends through the bore 66, the contact portion 50 of the clip 26 extends into the second groove 88 to releasably retain the nozzle 22a in that position. Thus, the nozzle 22a is releasably locked in its seated position. When the nozzle 22a is positioned outwardly with respect to the hand-piece 24, the contact portion 50 engages the first groove 86 to lock the nozzle 22a in its unseated position. Thus, the grooves 86 and 88 enable the nozzle 22a to be releasably locked in both unseated and seated positions. Preferably, the nozzle 22a of this embodiment is disposable (i.e., made of inexpensive materials) since the soluble substance 84 limits its effective life.

FIGS. 5 and 6 show another embodiment of a dental tool, designated generally at 20b, having a modified clip designated generally at 26b. In this embodiment, the contact portion of the clip 26 b comprises an annulus 90, made of an elastomeric material such as rubber, fixed to the clip 26b. The inner diameter of the annulus 90 is generally the same as the diameter of the nozzle 22 so that the annulus 90 frictionally engages the body portion 28 to releasably retain the nozzle 22 in the hand-piece 24. Also, the spring bias of the clip 26b causes the annulus to impart a lateral force to the body portion 28 to increase the retaining forces acting on the nozzle 22. By slightly deflecting the clip 26b, the lateral force acting on the body portion 28 can be cancelled and, therefore, the nozzle 22 can be removed from the hand-piece 24.

FIGS. 7 and 8 show another embodiment of a dental tool, designated generally at 20c, having a modified clip designated generally at 26c and a modified nozzle designated generally at 22c to prevent rotation of the nozzle 22c with respect to the hand-piece 24. The nozzle 22c is similar to the nozzle 22 shown in FIGS. 1-3 except the contact region 52c has a polygonal cross-section. The clip 26c is similar to the clip 26 shown in FIGS. 1-3 except the contact portion 50c has a serrated edge dimensioned to engage the contact region 52c. When engaged, the contact portion 50c and contact region 52c are locked together to prevent rotation of the nozzle 22c with respect to the hand-piece 24. Thus, the engagement of the serrated edge of the contact portion 50c with the polygonal-shaped contact region 52c constitutes means for preventing rotation of the nozzle 22c with respect to the hand-piece 24. When disengaged, however, the nozzle 22c is free to rotate about its longitudinal axis X.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A dental tool adapted to deliver a mixed stream of two fluids to teeth of a patient, the dental tool including a nozzle, a hand-piece, and a resiliently flexible clip adapted for releasably retaining the nozzle in the hand-piece, the nozzle having an elongate body portion, a proximal end, a distal end, and first and second conduits through the body portion defining first and second fluid passages, the hand-piece adapted for delivering a first fluid stream and a second fluid stream through a downstream end of the hand-piece to the proximal end of the nozzle and through the fluid passages and distal end of the nozzle, the clip having a base portion secured to the hand-piece and a contact portion engageable with a contact region of the nozzle's body portion, said clip adapted for being deflected to disengage said contact portion from said contact region to enable a user to readily remove the nozzle from or insert the nozzle into the hand-piece.

2. A dental tool in accordance with claim 1 further comprising means for preventing rotation of said nozzle relative to the hand-piece when said clip engages said body portion.

3. A dental tool in accordance with claim 1 wherein the contact portion of the clip prevents rotation of the nozzle relative to the hand-piece when the contact portion engages the contact region of the body portion, said nozzle being rotatable relative to the hand-piece when the contact portion of the clip is disengaged from the contact region of the body portion.

4. A dental tool in accordance with claim 3 wherein the contact portion of the clip has a serrated edge and wherein the cross-section of the contact region of the body portion is non-circular whereby engagement of the contact region by the contact portion prevents rotation of the nozzle relative to the hand-piece.

5. A dental tool in accordance with claim 4 wherein the cross-section of the contact region of the body portion is polygonal.

6. A dental tool in accordance with claim 1 wherein said contact portion of the clip is adapted for imparting a lateral force to said contact region of the body portion to frictionally secure the nozzle to the hand-piece when the proximal end is inserted in the hand-piece.

7. A dental tool in accordance with claim 1 further comprising a circumferential groove in said body portion, the contact portion of said clip being adapted to extend into said groove to releasably retain the nozzle in the hand-piece.

8. A dental tool in accordance with claim 1 wherein the nozzle is positionable between a seated position and an unseated position with the clip securing the nozzle to the hand-piece in both the seated and unseated positions, in the seated position the first fluid stream communicating with the first fluid passage and the second fluid stream communicating with the second fluid passage, in the unseated position the fluid streams mixing before entering into the first and second passages.

9. A dental tool in accordance with claim 8 further comprising first and second circumferential grooves in said body portion, said contact portion extending into the first groove when the nozzle is positioned in the seated position to releasably retain the nozzle in the seated position, said contact portion extending into the second groove when the nozzle is positioned in the unseated position to releasably retain the nozzle in the unseated position.

10. A dental tool in accordance with claim 8 wherein one of the conduits is coated with a substance, said substance being in communication with one of the fluid passages and soluble in a fluid from one of the fluid streams so that when the nozzle is in the unseated position said fluid communicates with the substance to dissolve it.

11. A dental tool in accordance with claim 10 wherein said soluble substance comprises a concentrated mouthwash.

12. A dental tool in accordance with claim 10 wherein said soluble substance comprises a disinfectant.

13. A dental tool in accordance with claim 1 wherein one of the conduits is coated with a substance, said substance being in communication with one of the fluid passages and soluble in a fluid from one of the fluid streams so that said substance dissolves when contacted by said fluid.

14. A dental tool in accordance with claim 13 wherein said soluble substance comprises a concentrated mouthwash.

15. A dental tool in accordance with claim 13 wherein said soluble substance comprises a disinfectant.

16. A dental tool in accordance with claim 1 wherein the first and second conduits have coaxial intake ports at the proximal end of the nozzle.

17. A dental tool of the type adapted to deliver a mixed stream of two fluids to teeth of a patient, the dental tool including a nozzle, a hand-piece, and a clip for removably connecting the nozzle to the hand-piece, the nozzle having an elongate body portion, a proximal end, a distal end, and first and second conduits through the body portion defining first and second fluid passages, the hand-piece adapted for delivering a first fluid stream and a second fluid stream through a downstream end of the hand-piece to the proximal end of the nozzle and through the fluid passages and distal end of the nozzle, the clip having a base portion secured to the hand-piece and a contact portion engageable with a contact region of the nozzle's body portion and imparting a lateral force thereto to frictionally secure the nozzle to the hand-piece when the proximal end is inserted in the hand-piece, said clip adapted for being resiliently deflected to disengage the contact portion of the clip from the contact region of the body portion to thereby enable a user to readily remove the nozzle from or insert the nozzle into the hand-piece.

18. A dental tool in accordance with claim 17 wherein the contact portion of the clip prevents rotation of the nozzle relative to the hand-piece when the contact portion engages the contact region of the body portion, said nozzle being rotatable relative to the hand-piece when the contact portion of the clip is disengaged from the contact region of the body portion.

19. A dental tool in accordance with claim 18 wherein the contact portion of the clip has a serrated edge and wherein the cross-section of the contact region of the body portion is non-circular whereby engagement of the contact region by the contact portion prevents rotation of the nozzle relative to the hand-piece.

20. A dental tool in accordance with claim 19 wherein the cross-section of the contact region of the body portion is polygonal.

21. A dental tool in accordance with claim 17 wherein the nozzle is positionable between a seated position and an unseated position with the clip securing the nozzle to the hand-piece in both the seated and unseated positions, in the seated position the first fluid stream communicating with the first fluid passage and the second fluid stream communicating with the second fluid passage, in the unseated position the fluid streams mixing before entering into the first and second passages.

22. A dental tool in accordance with claim 21 further comprising first and second circumferential grooves in said body portion, said contact portion extending into the first groove when the nozzle is positioned in the seated position to realeasably retain the nozzle in the seated position, said contact portion extending into the second groove when the nozzle is positioned in the unseated position to releasably retain the nozzle in the unseated position.

23. A dental tool in accordance with claim 21 wherein one of the conduits is coated with a substance, said substance being in communication with one of the fluid passages and soluble in a fluid from one of the fluid streams so that when the nozzle is in the unseated position said fluid communicates with the substance to dissolve it.

24. A dental tool in accordance with claim 23 wherein said soluble substance comprises a concentrated mouthwash.

25. A dental tool in accordance with claim 23 wherein said soluble substance comprises a disinfectant.

26. A dental tool of the type adapted to deliver a mixed stream of two fluids to teeth of a patient, the dental tool including a nozzle, a hand-piece, and a clip for removably connecting the nozzle to the hand-piece, the nozzle having an elongate body portion, a proximal end, a distal end, and first and second conduits through the body portion defining first and second fluid passages, the hand-piece adapted for delivering a first fluid stream and a second fluid stream through a downstream end of the hand-piece to the proximal end of the nozzle and through the fluid passages and distal, end of the nozzle, the clip having a base portion secured to the hand-piece and a contact portion engageable with a contact region of the nozzle's body portion and imparting a lateral force thereto to frictionally secure the nozzle to the hand-piece when the proximal end is inserted in the hand-piece, said contact portion being formed of an elastomeric material.

27. A dental tool in accordance with claim 26 wherein the contact portion comprises an elastomeric annulus positionable over said body portion.

* * * * *